(12) United States Patent
Fischheiter et al.

(10) Patent No.: US 11,391,676 B2
(45) Date of Patent: Jul. 19, 2022

(54) TEST ELEMENT ANALYSIS SYSTEM FOR THE ANALYTICAL EXAMINATION OF A SAMPLE

(71) Applicant: Roche Diagnostics Operations, Inc., Indianapolis, IN (US)

(72) Inventors: Lars Fischheiter, Ludwigsburg (DE); Reiner Stein, Bad Kreuznach (DE); Martin Goebel, Weinheim (DE)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 204 days.

(21) Appl. No.: 16/380,140

(22) Filed: Apr. 10, 2019

(65) Prior Publication Data
US 2019/0234884 A1    Aug. 1, 2019

Related U.S. Application Data

(63) Continuation of application No. PCT/EP2017/076030, filed on Oct. 12, 2017.

(30) Foreign Application Priority Data

Oct. 14, 2016    (EP) .................................... 16193898

(51) Int. Cl.
*G01N 21/78*    (2006.01)
*G01N 33/487*    (2006.01)
(Continued)

(52) U.S. Cl.
CPC ............. *G01N 21/78* (2013.01); *G01N 21/77* (2013.01); *G01N 21/8483* (2013.01);
(Continued)

(58) Field of Classification Search
CPC .... G01N 21/78; G01N 21/77; G01N 21/8483; G01N 33/487; G01N 2021/7723;
(Continued)

(56) References Cited

U.S. PATENT DOCUMENTS

| 4,720,372 A |   | 1/1988 | Fey et al. |
| 4,985,205 A | * | 1/1991 | Fritsche ............. G01N 21/8483 |
|  |   |  | 356/408 |

(Continued)

FOREIGN PATENT DOCUMENTS

| CN | 103575773 A | 2/2014 |
| JP | H04-364462 A | 12/1992 |

(Continued)

OTHER PUBLICATIONS

Hoenes, Joachim et al., The Technology Behind Glucose Meters: Test Strips, Diabetes Technology & Therapeutics, 2008, pp. S-10-S-26, vol. 10, Supplement 1.

(Continued)

*Primary Examiner* — Jennifer Wecker
*Assistant Examiner* — Oyeleye Alexander Alabi
(74) *Attorney, Agent, or Firm* — Roche Diagnostics Operations, Inc.

(57) ABSTRACT

A test element analysis system for analytical examination of a sample. The system comprises a measurement device, which comprises a test element receptacle for receiving at least one test element at least partially, wherein the receptacle comprises at least one first and at least one second part, wherein the first part comprises at least one support surface for placement of the test element, wherein the second part comprises at least one optical detector for detecting at least one detection reaction of at least one test chemical contained in the test element, wherein the second part is movable relative to the first part, wherein the receptacle is configured to position the second part such that a test element may be inserted into the receptacle and to subsequently position the second part in a closed position such that at least one abutment surface of the second part rests on the test element.

11 Claims, 6 Drawing Sheets

(51) Int. Cl.
*G01N 21/77* (2006.01)
*G01N 21/84* (2006.01)
*G01N 35/00* (2006.01)

(52) U.S. Cl.
CPC ... *G01N 33/487* (2013.01); *G01N 2021/7723* (2013.01); *G01N 2021/7759* (2013.01); *G01N 2021/7766* (2013.01); *G01N 2035/00128* (2013.01)

(58) Field of Classification Search
CPC ... G01N 2021/7759; G01N 2021/7766; G01N 2035/00128
See application file for complete search history.

(56) References Cited

U.S. PATENT DOCUMENTS

| | | | |
|---|---|---|---|
| 5,091,154 A | * | 2/1992 | Pauli ............... G01N 21/8483 356/244 |
| 5,281,395 A | | 1/1994 | Markart et al. |
| 7,558,624 B2 | | 7/2009 | Nishio |
| 2006/0128034 A1 | | 6/2006 | Petruno et al. |
| 2008/0257039 A1 | | 10/2008 | Thiel et al. |
| 2014/0285798 A1 | | 9/2014 | Nishimura |
| 2016/0187258 A1 | | 6/2016 | Mlekicki et al. |

FOREIGN PATENT DOCUMENTS

| | | |
|---|---|---|
| JP | 2016-161550 A | 9/2016 |
| WO | 2001/057502 A1 | 8/2001 |
| WO | 2010/058472 A1 | 5/2010 |
| WO | 2011/082344 A2 | 7/2011 |
| WO | 2013/076134 A1 | 5/2013 |
| WO | 2014/198700 A1 | 12/2014 |

OTHER PUBLICATIONS

International Search Report dated Nov. 22, 2017, in Application No. PCT/EP2017/076030, 3 pages.

Liu, Zhi-juan and Guo Bin, Review of Gas Test Technology of Hydrazine Rocket Propellant, China Academic Journal, 2007, pp. 37-42, vol. 25, No. 2.

* cited by examiner

TEST ELEMENT ANALYSIS SYSTEM FOR THE ANALYTICAL EXAMINATION OF A SAMPLE

CROSS-REFERENCE TO RELATED APPLICATIONS

This application is a continuation of International Patent Application No. PCT/EP2017/076030, filed 12 Oct. 2017, which claims the benefit of European Patent Application No. 16193898.0, filed 14 Oct. 2016, the disclosures of which are hereby incorporated herein by reference in their entirety.

TECHNICAL FIELD

The present disclosure relates to a test element analysis system for the analytical examination of a sample and a method for analytical examination of a sample, in particular, a body fluid. The devices and methods according to the present disclosure mainly may be used in the field of qualitatively or quantitatively detecting at least one analyte in a sample, such as a sample of a body fluid, and/or for determining at least one parameter of the sample. Other fields of application are feasible.

BACKGROUND

In the field of medical technology and diagnostics, a large number of devices and methods for determining the presence and/or the concentration of one or more analytes in samples, specifically fluid samples, such as body fluids, and/or for determining at least one parameter of a sample are known. Without restricting the scope of the present disclosure, in the following, mainly reference is made to the determination of coagulation parameters or analyte concentrations in blood samples, e.g., to the determination of blood glucose or ketone body concentrations. As an example, reference may be made to commercially available devices and systems, such as the Accu-Chek Active system, the Accu-Chek Mobile system, the Reflotron system or the cobas h 232 Point-of-Care-System, all by Roche Diagnostics GmbH, Germany. It shall be noted, however, that other types of samples or other types of analytes or parameters may be used in a similar way.

For performing fast and simple measurements, several types of test elements are known, which mainly are based on the use of one or more test chemicals, i.e., on the use of one or more chemical substances, one or more chemical compounds or one or more chemical mixtures, adapted for performing a detection reaction for detecting the analyte or determining the parameter. The test chemical often is also referred to as a test substance, a test reagent, a test chemistry or as a detector substance. For details of potential test chemicals and test elements comprising such test chemicals, which may also be used within the present disclosure, reference may be made to J. Hoenes et al.: The Technology Behind Glucose Meters: Test Strips, Diabetes Technology & Therapeutics, Vol. 10, Supplement 1, 2008, S-10 to S-26. Other types of test elements and/or test substances are feasible and may be used within the present disclosure.

By using one or more test chemicals, a detection reaction may be initiated, the course of which depends on the presence and/or the concentration of the at least one analyte or on the parameter to be determined. The detection reaction typically may be analyte-specific. Typically, as may also be the case in the present disclosure, the test chemical is adapted to perform at least one detection reaction when the analyte is present in the body fluid, wherein the extent and/or the degree of the detection reaction typically depends on the concentration of the analyte. Generally, the test chemical may be adapted to perform a detection reaction in the presence of the analyte, wherein at least one detectable property of at least one of the body fluid and the test chemical is changed due to the detection reaction. The at least one detectable property generally may be selected from a physical property and a chemical property. In the following, without restricting potential other embodiments, reference will mainly be made to detection reactions in which one or more physical properties are changed due to the detection reaction, such as one or more of at least one electrical property and at least one optical property. Further, without restricting alternative solutions, reference will be made to detection reactions in which at least one chemical property which is optically detectable is changed, i.e., to optical test elements. Other test elements, such as combined optical and electrical test elements, however, are usable, too.

One technical challenge in typical optical analyte measurement systems using a measurement device and a test element resides in an accurate and precise positioning of an optical detector relative to the test element, in particular to the test field of the test element. In typical optical measurement systems, a fixed distance is given between a supporting surface for the test element and the optical detector. A tolerance chain, however, between an optical detection area or test field of the test element and an optical system in the instrument is rather long and includes inter alia a positioning tolerance of the test element within the instrument, tolerances of the mechanical and optical parts of the instrument, and, additionally, tolerances of assembling. As a result of this chain, the total tolerance is rather high. Therefore, the depth of field of the measurement optics typically must be suited to cover a wide range, in order to ensure that the optical detection area of the test element is in focus every time when measurements are performed. These targets generally impose a strong limitation to the optical measurement systems.

A further challenge resides in the fact that, typically, various types of test elements exist. Thus, one and the same system may be used with various types of test elements. The test elements, however, typically vary in thickness. Thereby, the above-mentioned problem of bringing the test element in focus with the optical detector, i.e., bringing an optical detection area or test field of the test element within the focus range of the optical detector, is even more increased. The variations in the thickness of the test element add up to the tolerance chain and, thereby, additionally increase the technical challenges and requirements for the depth of field.

Despite the advantages achieved by the above-mentioned prior art technologies, several technical challenges remain. Thus, specifically, the device and method disclosed by WO 2011/082344 A2 typically requires an extensive time and effort for optimizing the positioning of the optical detector relative to the sample, including acquiring a plurality of images. Extensive computational algorithms are used which are rather resource-consuming. Further, the setup requires voluminous actors and space for sample movement which renders this technology rather unsuited for small handheld devices or even integrated laboratory devices.

BRIEF SUMMARY

It is against the above background that the embodiments of the present disclosure provide certain unobvious advantages and advancements over the prior art. In particular, the inventors have recognized a need for improvements in a test element analysis system and a method for analytical examination of a sample.

Although the embodiments of the present disclosure are not limited to specific advantages or functionality, it is noted that the present disclosure allows for a simple, precise and fast alignment of a test element relative to an optical detector.

In accordance with one embodiment of the present disclosure, a test element analysis system for the analytical examination of a sample is provided, comprising a measurement device, the measurement device comprising a test element receptacle for receiving at least one test element at least partially, wherein the test element receptacle comprises at least one first part and at least one second part, wherein the first part comprises at least one support surface for placement of the test element, wherein the second part comprises at least one optical detector for detecting at least one detection reaction of at least one test chemical contained in the test element, wherein the second part is movable relative to the first part, wherein the test element receptacle is configured to position the second part in at least one position such that a test element may be inserted into the test element receptacle and to subsequently position the second part in a closed position such that at least one abutment surface of the second part rests on the test element, wherein the test element analysis system further comprises at least one actuator for driving a relative movement of the first part and the second part, wherein the actuator is configured for performing a predetermined sequence of movements, sequentially bringing the second part into at least two positions, wherein the actuator is configured for stopping the movement in one of the at least two positions, respectively, and wherein the actuator is configured to move the second part towards the first part and to decouple as soon as the second part rests on the test element.

In accordance with another embodiment of the present disclosure, a method for analytical examination of a sample is provided, the method comprising: a) providing a measurement device having a test element receptacle for receiving at least one test element, wherein the test element receptacle comprises at least one first part and at least one second part, wherein the first part comprises at least one support surface for placement of the test element, wherein the second part comprises at least one optical detector for detecting at least one detection reaction of at least one test chemical contained in the test element, wherein the second part is movable relative to the first part, wherein the test element analysis system further comprises at least one actuator for driving a relative movement of the first part and the second part, wherein the actuator is configured for performing a predetermined sequence of movements, sequentially bringing the second part into at least two positions, wherein the actuator is configured for stopping the movement in one of the at least two positions, respectively, and wherein the actuator is configured to move the second part towards the first part and to decouple as soon as the second part rests on the test element; b) positioning the second part in a position such that a test element may be inserted into the test element receptacle; c) inserting the test element into the test element receptacle; d) closing the test element receptacle such that at least one abutment surface of the second part rests on the test element.

These and other features and advantages of the embodiments of the present disclosure will be more fully understood from the following description in combination with the drawings and the accompanying claims. It is noted that the scope of the claims is defined by the recitations therein and not by the specific discussion of features and advantages set forth in the present description.

BRIEF DESCRIPTION OF THE DRAWINGS

The following detailed description of the embodiments of the present disclosure can be best understood when read in conjunction with the following drawings, where like structure is indicated with like reference numerals and in which.

Figure 1:
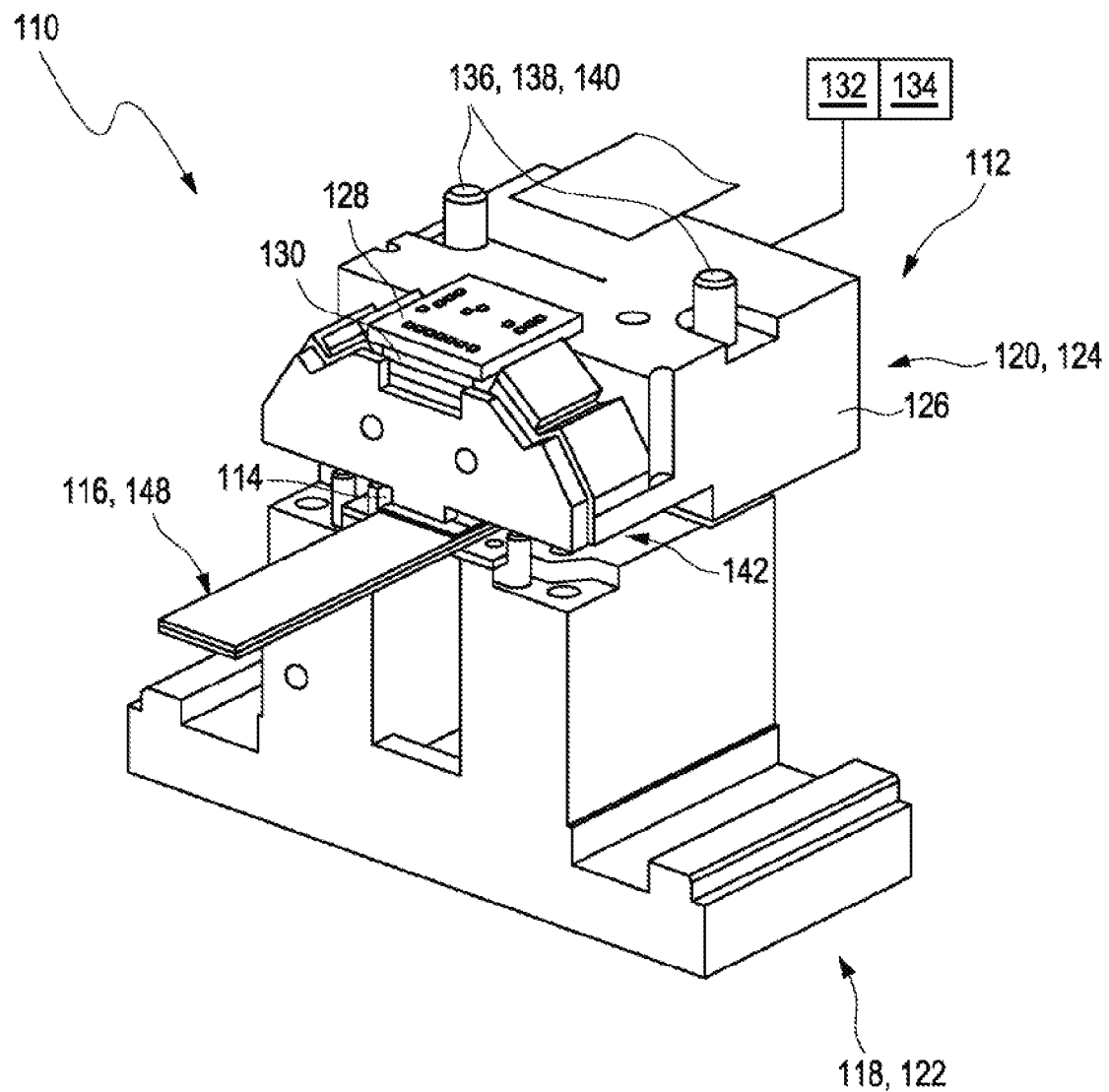
FIGS. 1A and 1B show details of an exemplary embodiment of a test element analysis system in a perspective view (FIG. 1A) and of a part of the test element analysis system in a cross-sectional view (FIG. 1B)

Skilled artisans appreciate that elements in the figures are illustrated for simplicity and clarity and have not necessarily been drawn to scale. For example, the dimensions of some of the elements in the figures may be exaggerated relative to other elements to help improve understanding of the embodiments of the present disclosure.

DETAILED DESCRIPTION

As used in the following, the terms "have", "comprise" or "include" or any arbitrary grammatical variations thereof are used in a non-exclusive way. Thus, these terms may both refer to a situation in which, besides the feature introduced by these terms, no further features are present in the entity described in this context and to a situation in which one or more further features are present. As an example, the expressions "A has B", "A comprises B" and "A includes B" may both refer to a situation in which, besides B, no other element is present in A (i.e., a situation in which A solely and exclusively consists of B) and to a situation in which, besides B, one or more further elements are present in entity A, such as element C, elements C and D or even further elements.

Further, it shall be noted that the terms "at least one", "one or more" or similar expressions indicating that a feature or element may be present once or more than once typically will be used only once when introducing the respective feature or element. In the following, in most cases, when referring to the respective feature or element, the expressions "at least one" or "one or more" will not be repeated, notwithstanding the fact that the respective feature or element may be present once or more than once.

Further, as used in the following, the terms "preferably", "more preferably", "particularly", "more particularly", "specifically", "more specifically", "typically", "more typically", or similar terms are used in conjunction with optional features, without restricting alternative possibilities. Thus, features introduced by these terms are optional features and are not intended to restrict the scope of the claims in any way. The disclosure may, as the skilled person will recognize, be performed by using alternative features. Similarly, features introduced by "in an embodiment of the disclosure" or similar expressions are intended to be optional features, without any restriction regarding alternative embodiments of the disclosure, without any restrictions regarding the scope of the disclosure and without any restriction regarding the possibility of combining the features introduced in such way with other optional or non-optional features of the disclosure.

As generally used within the present disclosure, the terms "patient" and "user" may refer to a human being or an animal, independent from the fact that the human being or animal, respectively, may be in a healthy condition or may suffer from one or more diseases. As an example, the patient or the user may be a human being or an animal suffering from diabetes. However, additionally or alternatively, the disclosure may be applied to other types of users or patients or diseases.

In a first aspect of the present disclosure, a test element analysis system for the analytical examination of a sample is disclosed. The test element analysis system comprises a measurement device. The measurement device comprises a test element receptacle for receiving at least one test element, specifically a test strip, at least partially, i.e., fully or partially. The test element receptacle comprises at least one first part and at least one second part. The first part comprises at least one support surface for placement of the test element. The second part comprises at least one optical detector for detecting at least one detection reaction of at least one test chemical contained in the test element. The second part is movable relative to the first part. Further, the test element receptacle is configured to position the second part in at least one position such that a test element may be inserted into the test element receptacle and to subsequently position the second part in a closed position such that at least one abutment surface of the second part rests on the test element.

As further used herein, the term "system" refers to an arbitrary set of interacting or interdependent component parts forming a whole. Specifically, the components may interact with each other in order to fulfill at least one common function. The at least two components may be handled independently or may be coupled or connectable. Thus, the term "test element analysis system" generally refers to a group of at least two elements or components which are capable of interacting with each other in order to perform at least one analytical detection, specifically at least one analytical detection of at least one analyte of the sample. The test element analysis system may generally also be referred to as an analytical system, an analytical kit, a sensor system or a measurement system.

As further used herein the term "sample" may refer to an arbitrary material or combination of materials taken for an analysis, testing or investigation. The sample may be a limited quantity of something which is intended to be similar to and represent a larger amount. However, the sample may also comprise a full specimen. The sample may be a solid sample, a liquid sample or a gaseous sample or a combination of these. Specifically, the sample may be a fluid sample, i.e., a sample which fully or partially is in a liquid state and/or in a gaseous state. A quantity of the sample may be describable in terms of its volume, mass or size. However, other dimensions are feasible. The sample may comprise only one material or only one compound. Alternatively, the sample may comprise several materials or compounds.

The term "analyte" generally refers to an arbitrary element, component or compound which may be present in the sample and the presence and/or the concentration of which may be of interest for the user, the patient or medical staff such as a medical doctor. Particularly, the analyte may be or may comprise an arbitrary chemical substance or chemical compound which may take part in the metabolism of the user or the patient, such as at least one metabolite. The detection of the at least one analyte specifically may be an analyte-specific detection.

As further used herein, the term "body fluid" may refer to a fluid which typically is present in a body or body tissue of the user or the patient and/or which may be produced by the body of the user or the patient. As an example for body tissue, interstitial tissue may be named. Thus, as an example, the body fluid may be selected from the group consisting of blood and interstitial fluid. However, additionally or alternatively, one or more other types of body fluids may be used, such as saliva, tear fluid, urine or other body fluids. Thus, specifically, as will be outlined in further detail below, the sensor may be configured for detecting at least one analyte in a body tissue.

The term "analytical examination" generally may refer to a process of determining the presence and/or the quantity and/or the concentration of the at least one analyte or to a process of determining a parameter of the sample which is characteristic of the properties of the sample, e.g., glucose. The analytical examination may be or may comprise a qualitative detection, simply determining the presence of the at least one analyte or the absence of the at least one analyte, and/or may be or may comprise a quantitative detection, which determines the quantity and/or the concentration of the at least one analyte. As a result of the detection, at least one signal may be produced which characterizes an outcome of the detection, such as at least one measurement signal. The at least one measurement signal specifically may be or may comprise and/or may fully or partially be transformed into at least one electronic signal such as at least one voltage and/or at least one current. The at least one signal may be or may comprise at least one analogue signal and/or may be or may comprise at least one digital signal.

As described above, the measurement device comprises the test element receptacle for receiving the at least one test element at least partially. The test element analysis system may further comprise at least one test element. The term "test element" may generally refer to an arbitrary device which is capable of detecting the analyte in the sample or of determining the parameter of the sample. The test element may specifically be a strip-shaped test element. As used herein, the term "strip-shaped" refers to an element having an elongated shape and a thickness, wherein an extension of the element in a lateral dimension exceeds the thickness of the element, such as by at least a factor of 2, typically by at least a factor of 5, more typically by at least a factor of 10 and most typically by at least a factor of 20 or even at least a factor of 30. Thus, the test element may also be referred to as test strip.

The test element may have at least one carrier and at least one test chemical for performing at least one detection reaction in the presence of an analyte contained in the sample. As further used herein, the term "carrier" may refer to an arbitrary element, such as a planar element, which is configured to hold or to carry another object. Thus, the carrier may also be referred to as substrate. Further, the carrier may specifically be a strip-shaped carrier. The term "test chemical", also referred to as a test chemistry, may refer to an arbitrary material or a composition of materials adapted to change at least one detectable property in the presence of the analyte. Specifically, this property may be an optically detectable property, such as a color change and/or a change in remissive properties. Specifically, the test chemical may be a highly selective test chemical, which only changes the property if the analyte is present in the sample of the body fluid applied to the test element, whereas no change occurs if the analyte is not present. More typically, the degree or change of the property may be dependent on the concentration of the analyte in the body fluid, in order to allow for a quantitative detection of the analyte. Exemplarily, the test chemical may be a dry test chemical. As further used herein, the term "dry" may refer to a property of an arbitrary chemical of being at least to a large extent free from moisture.

The test chemical may specifically be configured for performing at least one optically detectable detection reaction. As used herein, the term "optically detectable detection reaction" refers to a detection of an optical detectable property of the analyte itself or an auxiliary compound which is produced or converted with a detection reaction depending on the presence and/or concentration of the analyte in the sample, such as a color change and/or a change in remissive properties. The optically detectable detection reaction may be analyte specific. Further, the optically detectable detection reaction may be a qualitative and/or a quantitative detection.

Exemplarily, the test element may have at least one test field comprising the at least one test chemical. As further used herein, the term "test field" may refer to an arbitrary area or region of an object wherein an arbitrary measurement, specifically an analytical measurement, is conducted. Specifically, the test field may be capable of performing at least one change being characteristic for an analyte or a parameter. The test chemical as described above may be located within the test field, particularly on at least one surface of the test field. Thus, the test field may also be referred to as measuring zone or measuring field. Further, the test element may comprise at least one capillary configured for receiving the sample. The term "capillary" generally refers to an arbitrary small, elongate void volume such as a small tube. Generally, the capillary may comprise dimensions in the millimeter or sub-millimeter range. Commonly, a fluidic medium may migrate through the capillary by capillary action wherein the fluidic medium may flow in narrow spaces of the capillary without an assistance of external forces like gravity due to intermolecular forces between the fluidic medium and a surface of the capillary facing the fluidic medium.

As described above, the test element analysis system comprises the measurement device. As further used herein, the term "measurement device" may refer to an arbitrary device, typically an electronic device, which is configured to detect at least one signal. The signal may be an optical signal and/or an electrochemical signal. The measuring device may be handled independently from the test element and may be adapted to interact with the test element in order to perform an analysis, such as by detecting the at least one signal. Thus, the term "measurement device" may often also be referred to as a measuring device, as an analytical device, as a meter or as a test device. The measurement device may further comprise at least one evaluation device for evaluating at least one measurement performed with the measurement device, specifically at least one processor. As further used herein, the term "evaluation device" may refer to an arbitrary device being configured to derive at least one item of information from data. Specifically, the evaluation device may be configured to derive the at least one item of information regarding the presence and/or concentration of the analyte in the body fluid or a parameter of the body fluid from at least one signal.

As described above, the measurement device comprises the test element receptacle for receiving the at least one test element at least partially. As further used herein, the term "receptacle" may generally refer to a free volume of an arbitrary element which is configured to at least partially receive or hold another object. Thus, the receptacle may have a shape which corresponds to the other object or vice versa. Exemplarily, the other object, or at least an insertable portion of the other object may have a rectangular shape and the receptacle may have a rectangular shape as well. The term "test element receptacle" generally may refer to an arbitrary receptacle which is configured to receive or to hold an arbitrary test element. The test element receptacle may have an elongated shape extending along a longitudinal axis. Thus, the test element receptacle may provide an elongated channel or opening having a cross-section which at least widely corresponds to the cross-section of the test element and into which the test element may be inserted. Other embodiments may be feasible. The test element may specifically be configured to be put reversibly into the test element receptacle. Specifically, the test element may be configured to be positioned on a specific position within the test element receptacle such that a movement of the test element in at least one direction may be suppressed at least to a large extent. Thus, the test field of the test element may be located in a predetermined position relative to the measurement device. Further, inside the test strip receptacle, one or more ports or interfaces may be provided for electrically and/or optically contacting the test strip. The interfaces may exemplarily be or may comprise one or more ports. Additionally or alternatively, other kinds of interfaces may be feasible.

Further, the test element receptacle may comprise at least one positioning element. Further, the positioning element may be an ejector element. The positioning element may be configured for limiting an insertion of the test element into the test element receptacle. Specifically, the positioning element may be movable in a direction of insertion of the test element and the positioning element may be configured for ejecting the test element after use, when the test element receptacle is in the open position.

As described above, the test element receptacle comprises at least one first part and at least one second part. As further used herein, the term "part" refers to an arbitrary component of an object. Thus, several components interact with each other and may form a whole. The components of the object may be handled independently or may be coupled or connectable to each other. The terms "first part" and "second part" may be considered as nomenclature only, without numbering or ranking the named elements, without specifying an order and without excluding a possibility that several kinds of first parts and second parts may be present. Further, additional parts such as one or more third parts may be present.

As described above, the first part comprises the support surface for placement of the test element. As further used herein, the term "support surface" refers to an arbitrary surface which is configured to hold an arbitrary element. Specifically, the support surface may be configured to establish a close connection to the element. Therefore, the element may be configured to lie slackly on the support surface. Thus, the support surface may be an essentially flat surface. Specifically, the abutment surface may be essentially parallel to the support surface. Thereby, the term "essentially parallel" may refer to a property of the abutment surface of being parallel to the support surface. Exemplarily, the abutment surface may be exactly parallel to the support surface. However, small deviations may be feasible. Specifically, the abutment surface may be arranged at an angle of ±20°, typically of ±10°, more typically of ±5° to the support surface.

As described above, the second part comprises the at least one optical detector for detecting the at least one detection reaction of the at least one test chemical contained in the test element. As further used herein, the term "detector" may refer to an arbitrary device which is configured to detect events or changes in its environment and to provide a corresponding output. The term "optical detector" may generally refer to an arbitrary optical instrument configured for receiving electromagnetic radiation, typically light in the infrared and/or visible and/or ultraviolet spectral range. Thus, the optical detector may be configured for recording images, which may be stored locally, transmitted to another location or both. The optical detector may comprise at least one light source and at least one photo detector. Further, the optical detector may comprise at least one lens element. The abutment surface may be located in one or both of a focal plane of the lens element and/or an essentially ideal object plane of the optical detector.

As outlined above, the abutment surface may be located in the essentially ideal object plane of the optical detector. The term "object plane" may refer to a plane which is perpendicular to an optical axis in case of an imaging optical system and which may comprise at least one object point. Thus, when the second part rests on the test element, the test field may be in focus with the optical detector. In ideal cases, all object points which are located in one object plane are projected on one image plane. However, due to aberrations the image plane may be curved. Thus, as used herein, the term "essentially ideal object plane" may refer to a plane which is essentially perpendicular to the optical axis, such as with a tolerance of ±10°, typically of ±5°, more typically of ±1°. Thus, when the abutment surface rests on the test element, the test field of the test element may be in focus with the optical detector.

The lens element may be located in front of one or both of the at least one light source or the at least one photo detector. The detector may be fully or partially comprised in the second part. Specifically, the optical detector may be fixed positioned within the second part. The optical detector may be configured to evaluate further optical information on the test element. Exemplarily, the test element may have a bar code and the optical detector may be configured to evaluate the bar code. The optical detector may be configured to evaluate the further optical information in combination with detecting the at least one detection reaction of the at least one test chemical contained in the test element. Alternatively, the optical detector may be configured to evaluate the further optical information separately from detecting the at least one detection reaction of the at least one test chemical contained in the test element.

Further, as described above, the second part comprises the at least one abutment surface. As further used herein, the term "abutment surface" may refer to a surface of an arbitrary element which is configured to support an object which is positioned onto the surface. Thereby, the abutment surface may specifically be or may comprise a flat, elongate surface providing a contact surface for the test element. Further, a movement of the test element may be prevented at least to a large extent in at least one direction. The abutment surface may rest flatly on the test element, specifically on the cover of the test element when the test element receptacle is closed.

When the second part is moved relative to the first part, the abutment surface must not necessarily be essentially parallel to the carrier of the test element. In the closed position it is essentially parallel to the carrier of the test element by clamping the carrier of the test element between the abutment surface located on the second part and the support surface of the first part. Thereby, the term "essentially parallel" may refer to a property of the abutment surface of being parallel to the carrier. Exemplarily, the abutment surface may be exactly parallel to the carrier. However, small deviations may be feasible. Specifically, the abutment surface may be arranged at an angle of ±20°, typically of ±10°, more typically of ±5° to the carrier. Consequently, a chain of errors may be reduced, which may exemplarily result from a swelling of the test chemical.

Specifically, the abutment surface may be arranged next to the test field having the test chemical. Further, the abutment surface may be separated from the test field. Thus, the test chemical may be located on the front side of the test element and test element analysis system may be configured to operate independently from a thickness of the test chemical, exemplarily in case of a swelling of the test chemical as outlined above. The separation of the abutment surface from the test chemical may lead to an increased hygiene as an entrainment or carry-over of the test chemical from the test element to the test element analysis system is avoided or at least reduced to a large extent. Further, a deforming or bending of the test field is avoided or at least reduced to a large extent.

Further, the second part may comprise at least two abutment surfaces, typically at least three abutment surfaces. The abutment surface may have a rectangular or a round shape. However, other shapes may also be feasible. Exemplarily, the abutment surface may have a U-shape which may at least partially surround the test field. Thereby, the U-shaped abutment surface may surround the test field on at least three sides of the test field. Further, exemplarily, the abutment surface may completely surround the test field. Thereby, the abutment surface may have a recess or a gap within an interior region of the abutment surface and the test field is located within the recess or gap. Exemplarily, the abutment surface may be ring-shaped. The U-shaped abutment surface and the completely surrounding abutment surface may lead to an increased stabilizing effect, as a movement of the test element in several directions may be prevented or at least reduced to a large extent.

As described above, the second part is movable relative to the first part. Exemplarily, the first part may rest while the second part moves. Alternatively, the first part may move and the second part rests. Moreover, the first part and the second part may move, respectively. Specifically, the second part may be moveable relative to the first part in a direction essentially perpendicular to the support surface. Exemplarily, the first part may be moveable relative to the second part in a direction essentially perpendicular to the support surface. Thereby, the term "essentially perpendicular" may refer to a state wherein the first part and the second part are positioned exactly perpendicular to each other or with a slight deviation from the exact perpendicular position. Specifically, the second part may be moveable at an angle of 90°±30°, typically at an angle of 90°±20°, more typically of 90°±10°, even more typically of 90°±5°, relative to the first part.

Due to the movement in a direction essentially perpendicular to the support surface an accurate and exact alignment of the test element and specifically of the test field comprising the test chemical may be ensured. The test element analysis system may be configured such that the test element may be positioned on the first part before the second part is positioned and moved towards the first part. Thus, a canting or a lateral displacement of the test element may be avoided or reduced at least to a large extent. Thus, a reliable measurement may be feasible.

Further, the test element receptacle may comprise at least one guiding element for guiding a relative movement of the second part and the first part. The guiding element may be part of the lateral guiding or vice versa. As further used herein, the term "guiding element" may refer to an arbitrary element which is configured to support a movement of another object within a desired direction. Specifically, the guiding element may comprise at least one guide rail, more typically at least one linear guide rail.

Specifically, the first part may form a fixed subassembly and the second part may form a moveable subassembly of the test element receptacle. As further used herein, the term "subassembly" may refer to a component or a group of components which form part of a whole assembly, specifically of a device. Further, the term "moveable subassembly" may refer to a subassembly which is moveable in at least one direction, specifically relative to another subassembly. The optical detector may be inserted into at least one cavity within the moveable subassembly. On the contrary, the term "fixed subassembly" may refer to a subassembly which may stay or rest in a position, specifically in a desired position, such that a movement of the subassembly may be prevented at least to a large extent. Specifically, the second part may be moveable in a linear fashion relative to the first part.

Specifically, the movable subassembly may comprise at least one moveable block and the optical detector may be inserted into the moveable block. The term "block" may generally refer to an arbitrary element which may be made of a solid material. Specifically, the block may have a rectangular or a cubic shape. Still, other embodiments are feasible. The moveable block may be moveable in a linear fashion. The term "moveable in a linear fashion" may refer to a property of an arbitrary element of being capable of being moved in a straight manner such as on a virtual straight line. Thereby, the virtual straight line may be at least essentially free from bends. Further, the term "moveable in a linear fashion" may refer to a property of an arbitrary element of being capable of being moved in a constant manner such as with a constant velocity.

The second part may further comprise at least one alignment pin for engagement with at least one alignment hole. Specifically, the alignment hole may be part of the test element. Specifically, the second part may comprise the block which is linearly moveable in a direction towards the first part and the alignment pin may be partially embedded into the block. Further, the alignment pin may be configured to position the test element relative to the at least one optical detector. As further used herein, the term "pin" may refer to an arbitrary element which is configured for fastening another object. Therefore, the pin may specifically have an elongate shape and may further have a tip which is configured to rest on a surface. The term "alignment pin" may generally refer to an arbitrary pin which is configured to arrange another object in a desired position and to prevent at least to a large extent a movement of the object in at least one position. The alignment pin may specifically be or may comprise a cylindrical alignment pin, typically a cylindrical alignment pin having a circular cross-section. Further, the alignment pin may have at least one tip, specifically at least one tapered tip. As further used herein, the term "alignment hole" may refer to an arbitrary hole within an element which is configured for an arrangement of the element within a desired position. Thereby, a movement of the element may be prevented at least to a large extent in at least one direction. The alignment hole may be specifically configured to be penetrated by an object which is configured to fix hold the element within at least one position. Specifically, the alignment hole may have a shape and a cross-section which correspond to the alignment pin, respectively.

As described above, the test element receptacle is configured to position the second part in at least one position such that the test element may be inserted into the test element receptacle and to subsequently close the test element receptacle such that the abutment surface of the second part rests on the test element. Generally, the term "position" may generally refer to a spatial location of an object. Further, the term "positioning" may refer to an arbitrary process of bringing an object into a desired position such as by moving the object into the desired position. Further, the term "inserting" may refer to a process of placing an arbitrary element at least partially into another object such as into a receptacle of the object. Beyond, the term "closing" may refer to an arbitrary process of sealing an arbitrary subject, specifically a cavity or a hole of the subject, such that a removing of another element which is at least partially received in the cavity or in the hole of the subject, is prevented at least to a large extent. The term "resting" may refer to a property of an element of staying on or within another object. Thereby, a movement of the element relative to the object may be prevented at least to a large extent. Specifically, the element may be configured to stay on or within the other object without any substantial additional contact pressure.

The test element receptacle may be configured to position the second part in at least two distinct positions relative to the first part. The at least two distinct positions may comprise an open position for inserting the test element into the test element receptacle and/or removing the test element from the test element receptacle and a closed position for performing a measurement. The terms "closed position" and "open position" may be considered as nomenclature only, without numbering or ranking the named elements, without specifying an order and without excluding a possibility that several kinds of closed positions and open positions may be present. Further, additional positions may be present.

The term "open position" may refer to a position wherein the first part and the second part are spaced apart such that the test element may freely be inserted into the test element receptacle. One or more than one open position may be given. Specifically, the alignment pin may be positioned such that the test element is sliding over the alignment pin during the insertion, until the alignment pin snaps into the alignment hole of the test element. During the insertion, the test element may be deformed by the alignment pin, until the alignment pin snaps into the alignment hole of the test element. As further used herein, the term "being deformed" may refer to a property of an arbitrary element of having an altered shape which differs from an original shape of the element and wherein the altered shape is based on an external force applied to the element such as a mechanical force. Exemplarily, the original shape of the element may correspond to a plane shape and the altered shape may comprise a bent of the element caused by the mechanical force. Further, the term "open position" may refer to a position wherein the first part and the second part are spaced apart such that the test element may freely be removed from the test element receptacle. Specifically, in the open position, the alignment pin may be pulled out of the alignment hole completely. The terms "being freely inserted" and "being freely removed" may generally refer to a property of an arbitrary element of being at least partially placed into another object or of being taken from the other object without or at least almost without any resistance, specifically such that a user may be enabled to insert or to remove the element by applying only minor forces.

As further used therein, the term "closed position" may refer to a state, wherein the first part and the second part are arranged relative to each other such that a removal of the test element from the test element receptacle is prevented at least to a large extent. In the closed position, the test element may be supported by the first part and the second part may rest on the test element. The test element analysis system may be configured to perform a measurement when the test element is inserted into the receptacle and the second part is in the closed position. Thereby, the term "performing a measurement" may refer to a property of an arbitrary device of detecting at least one signal. Exemplarily, the signal may be an optical signal. Specifically, the signal may be utilized to determining the presence and/or the quantity and/or the concentration of the at least one analyte as described above. Specifically, the alignment pin may protrude through the alignment hole of the test element.

Further, the test element analysis system may comprise at least one actuator for driving a relative movement of the first part and the second part. As further used herein, the term "actuator" refers to an arbitrary element which is configured to move or control a mechanism or a system. Specifically, the actuator may be configured to move the second part from the open position to the closed position and vice versa. The actuator may be operated by a source of energy, typically electric current or mechanical pressure and may convert energy into motion. The actuator may be selected from the group consisting of: a mechanical actuator, an electromagnetic actuator, a pneumatic actuator. However, other kinds of actuators may be applied.

The actuator may be configured for performing a predetermined sequence of movements, sequentially bringing the second part into at least two positions, specifically into the closed position and into the open position. Further, the actuator may be configured for stopping the movement in one of the at least two positions, respectively. Further, the actuator may be configured to move the second part towards the first part and to decouple as soon as the second part rests on the test element. Thus, the test element analysis system may be configured such that the second part is actively moved towards the first part. As an example, the actuator may be configured to move the second part downwards, towards the test element, such that the second part contacts the test element and, as soon as the seconds part contacts the test element or rests on the test element, the second part may be decoupled from the actuator, such that a further downward movement of the second part is prevented.

Specifically, the actuator may be configured for stopping the movement in the closed position and in the open position, respectively. Further, the test element analysis system may comprise at least one controller for controlling the predetermined sequence of movements. Beyond, the second part may be biased by at least one spring element against the first part, wherein the actuator is configured to act against the bias.

Due to the decoupling of the actuator as described above, a contact pressure may be defined by a weight of the second part. Thus, the abutment surface may be configured to provide a mechanical support for the test element by resting on the test element, specifically on the front side of the test element. An additional active pressure caused by the actuator may be avoided. Thus, a bending of the test element in the closed position may be avoided or at least reduced to a large extent. Further, a canting and/or a deformation of the test element may be avoided or reduced at least to a large extent which could bring the test field outside of a perfect optical plane. Thus, a reliable measurement may be feasible.

In a further aspect of the present disclosure, a method for analytical examination of a sample, in particular of a body fluid, is disclosed. The method may comprise using the test element analysis system as described above or as will further be described below. The method comprises the method steps as given in the independent claims and as listed as follows. The method steps may be performed in the given order. However, other orders of the method steps are feasible. Further, one or more of the method steps may be performed in parallel and/or on a timely overlapping fashion. Further, one or more of the method steps may be performed repeatedly. Further, additional method steps may be present which are not listed.

The method for analytical examination of a sample comprises the following steps:

a) providing a measurement device having a test element receptacle for receiving at least one test element, wherein the test element receptacle comprises at least one first part and at least one second part, wherein the first part comprises at least one support surface for placement of the test element, wherein the second part comprises at least one optical detector for detecting at least one detection reaction of at least one test chemical contained in the test element wherein the second part is movable relative to the first part;

b) positioning the second part in a position such that a test element may be inserted into the test element receptacle;

c) inserting the test element into the test element receptacle;

d) closing the test element receptacle such that at least one abutment surface of the second part rests on the test element.

Specifically, after performing step b), the test element, specifically the test field, may be out of focus with the detector, and after performing step d), the test element, specifically the test field, will be in focus with the detector. In step d), the optical detector is moved towards the test element. As used herein, the term "closing" may refer to a process, wherein the first part and the second part approach each other and not to a process of completely closing the test element receptacle. Further, step d) may exemplarily be triggered by a light barrier. The light barrier may specifically be configured to recognize that the test element is inserted into the test element receptacle. Further, the method may comprise:

e) performing at least one analytical measurement by using the optical detector for detecting at least one detection reaction of at least one test chemical contained by the test element.

The step of performing the analytical measurement may specifically be performed after method step d). Further, the method may comprise:

f) positioning the second part in an open position, wherein in the open position the first part and the second part are spaced apart, and g) removing the test element from the test element receptacle.

Steps f) and g) may specifically be performed after steps d) or e). Exemplarily, the removing of the test element from the test element receptacle of the test element analysis system may be supported by tilting the test element analysis system by the user or the patient or by applying a small physical effort onto the test element by the user or the patient. However, other embodiments may be feasible.

The proposed test element analysis system for the analytical examination of a sample as well as the proposed method for analytical examination of a sample provide many advantages over known devices and methods.

Usually, in a common test element analysis system based on an optical measurement system there may be a fixed distance between the support surface for the test element and the optical detector. Usually, a tolerance chain between the test field of the test element, specifically of an optical detection area of the test element, and the optical detector may be very long (position tolerance of the test element plus production tolerances of the first part and the second part plus assembly tolerances). As a result of this chain, the tolerance itself may be very high. Therefore, generally, a depth of field of the optical detector should cover a wide range, specifically to ensure that the test field of the test element is in focus every time. Thus, this may be a limitation of the optical detector.

In case the test element analysis system is configured to operate with several test element systems, wherein the several test elements have different thicknesses, respectively, the challenge as described above may increase. Specifically, variations in the thickness may be additional to the tolerance chain as described above. Thus, a requirement for the depth of field may increase once more.

The test element analysis system according to the present disclosure may have the optical detector, wherein a distance between the optical detector and the test field of the test element is fixed. This may be realized in a way that the optical detector is movable in a direction of an optical axis of the optical detector. An end position may float without a hard stop limitation in the test element analysis system itself. The relative distance of components within the optical detector itself, i.e., lens, sensor, filters, illumination, may remain fixed. A reference area that defines the end position for the optical detector may not be the support surface of the measurement device, but rather an area on a top side of the test element which may also be a reference of the test field of the test element.

In the closed position, the second part may be configured to slide down until a reference area and/or the abutment surface of the second part gets in touch with the reference area of the test element. The end position of the optical detector relative to the test field inside the test element may therefore be independent of a thickness of the test element.

Variations in the thickness of the test element and most of the assembly tolerances may not be relevant for the optical detection at least to a large extent, specifically as these variations may be covered by the design of an optical detector according to the present disclosure. Therefore, the tolerance chain between the test field inside the test element and the optical detector may be very short.

It may be advantageous that the support surface of the test element inside the test element analysis system, specifically inside the test element receptacle, may be flat. A height difference between the area for optical detection on the test strip which corresponds typically to the test field of the test element and the reference area on the test strip getting in contact with the abutment surface of the second part may be prevented at least to a large extent by such an extended flat support surface of the test receptacle of the test element analysis system. Therefore, it may be advantageous to use only one part for both areas of this support surface. Also other functions, like heating of the test element, can be achieved by such a support surface, resulting, e.g., in a receptacle comprising a flat heating element as a support surface or a test element.

Summarizing the findings of the present disclosure, the following embodiments are typical:

Embodiment 1: A test element analysis system for the analytical examination of a sample, comprising a measurement device, the measurement device comprising a test element receptacle for receiving at least one test element, specifically a test strip, at least partially, wherein the test element receptacle comprises at least one first part and at least one second part, wherein the first part comprises at least one support surface for placement of the test element, wherein the second part comprises at least one optical detector for detecting at least one detection reaction of at least one test chemical contained in the test element, wherein the second part is movable relative to the first part, wherein the test element receptacle is configured to position the second part in at least one position such that a test element may be inserted into the test element receptacle and to subsequently position the second part in a closed position such that at least one abutment surface of the second part rests on the test element.

Embodiment 2: The test element analysis system according to the preceding embodiment, wherein the optical detector comprises at least one lens element, wherein the abutment surface is located in one or both of a focal plane of the lens element, an essentially ideal object plane of the optical detector.

Embodiment 3: The test element analysis system according to any one of the preceding embodiments, wherein the optical detector comprises at least one light source and at least one photo detector.

Embodiment 4: The test element analysis system according to the two preceding embodiments, wherein the lens element is located in front of one or both of the at least one light source or the at least one photo detector.

Embodiment 5: The test element analysis system according to any one of the preceding embodiments, wherein the optical detector is fixedly positioned within the second part.

Embodiment 6: The test element analysis system according to any one of the preceding embodiments, wherein the second part is movable relative to the first part in a direction essentially perpendicular to the support surface.

Embodiment 7: The test element analysis system according to any one of the preceding embodiments, wherein the test element analysis system further comprises at least one test element having at least one carrier and the at least one test chemical for performing at least one detection reaction in the presence of an analyte contained in the sample, specifically glucose or ketone bodies.

Embodiment 8: The test element analysis system according to the preceding embodiment, wherein the test element is a test strip.

Embodiment 9: The test element analysis system according to any one of the two preceding embodiments, wherein the test element has at least one test field comprising the at least one test chemical.

Embodiment 10: The test element analysis system according to the preceding embodiment, wherein the test chemical is configured for performing at least one optically detectable detection reaction.

Embodiment 11: The test element analysis system according to any one of the four preceding embodiments, wherein the test chemical is a dry test chemical.

Embodiment 12: The test element analysis system according to any one of the five preceding embodiments, wherein the carrier is a strip-shaped carrier.

Embodiment 13: The test element analysis system according to any one of the six preceding claims, wherein the abutment surface flatly rests on the carrier when the abutment surface rests on the test element.

Embodiment 14: The test element analysis system according to any one of the seven preceding embodiments, wherein, when the second part is moved relative to the first part, the abutment surface always is parallel to the support surface.

Embodiment 15: The test element analysis system according to any one of the preceding embodiments, wherein the second part further comprises at least one alignment pin for engagement with at least one alignment hole of the test element.

Embodiment 16: The test element analysis system according to the preceding embodiment, wherein the second part comprises a block which is linearly movable in a direction towards the first part, wherein the alignment pin is partially embedded into the block.

Embodiment 17: The test element analysis system according to any one of the two preceding embodiments, wherein the alignment pin is configured to position the test element relative to the at least one optical detector.

Embodiment 18: The test element analysis system according to any one of the preceding embodiments, wherein the test element receptacle is configured to position the second part in at least two distinct positions relative to the first part, the at least two distinct positions comprising a closed position for performing a measurement and an open position for at least one of removing the test element from the test element receptacle and for inserting the test element into the test element receptacle.

Embodiment 19: The test element analysis system according to the preceding embodiment, wherein in the closed position the test element is supported by the first part and the second part rests on the test element.

Embodiment 20: The test element analysis system according to any one of the preceding embodiments, wherein the at least one optical detector is fully or partially comprised in the second part.

Embodiment 21: The test element analysis system according to any one of the preceding embodiments, wherein the support surface is an essentially flat surface.

Embodiment 22: The test element analysis system according to the preceding embodiment, wherein the abutment surface is essentially parallel to the support surface.

Embodiment 23: The test element analysis system according to any one of the preceding embodiments, wherein the test element receptacle contains at least one guiding element for guiding a relative movement of the second part and the first part.

Embodiment 24: The test element analysis system according to the preceding embodiment, wherein the guiding element comprises at least one guide rail, more preferably at least one linear guide rail.

Embodiment 25: The test element analysis system according to any one of the preceding embodiments, wherein the test element analysis system further comprises at least one actuator for driving a relative movement of the first part and the second part.

Embodiment 26: The test element analysis system according to the preceding embodiments, wherein the actuator is configured for performing a predetermined sequence of movements, sequentially bringing the second part into at least two positions.

Embodiment 27: The test element analysis system according to the preceding embodiment, wherein the actuator is configured for stopping the movement in one of the at least two positions, respectively.

Embodiment 28: The test element analysis system according to any one of the two preceding embodiments, wherein the test element analysis system comprises at least one controller for controlling the predetermined sequence of movements.

Embodiment 29: The test element analysis system according to any one of the four preceding embodiments, wherein the second part is biased by at least one spring element against the first part, wherein the actuator is configured to act against the bias.

Embodiment 30: The test element analysis system according to any one of the preceding embodiments, wherein the test element receptacle further comprises at least one positioning element, wherein the positioning element is configured for limiting an insertion of the test element into the test element receptacle.

Embodiment 31: The test element analysis system according to the preceding embodiment, wherein the positioning element is movable in a direction of insertion of the test element, wherein the positioning element is configured for ejecting the test element after use.

Embodiment 32: The test element analysis system according to any one of the preceding embodiments, wherein the first part forms a fixed subassembly and wherein the second part forms a movable subassembly of the test element receptacle.

Embodiment 33: The test element analysis system according to the preceding embodiment, wherein the optical detector is inserted into at least one cavity within the movable subassembly.

Embodiment 34: The test element analysis system according to any one of the two preceding embodiments wherein the movable subassembly comprises at least one movable block, wherein the optical detector is inserted into the movable block.

Embodiment 35: The test element analysis system according to any one of the preceding embodiments, wherein the measurement device further comprises at least one evaluation device for evaluating at least one measurement performed with the measurement device, specifically at least one processor.

Embodiment 36: A method for analytical examination of a sample, in particular a body fluid, the method comprising
  a) providing a measurement device having a test element receptacle for receiving at least one test element, wherein the test element receptacle comprises at least one first part and at least one second part, wherein the first part comprises at least one support surface for placement of the test element, wherein the second part comprises at least one optical detector for detecting at least one detection reaction of at least one test chemical contained in the test element, wherein the second part is movable relative to the first part;
  b) positioning the second part in a position such that a test element may be inserted into the test element receptacle;
  c) inserting the test element into the test element receptacle;

d) closing the test element receptacle such that at least one abutment surface of the second part rests on the test element.

Embodiment 37: The method according to the preceding embodiment, wherein the method comprises using the test element analysis system according to any one of the preceding claims referring to a test element analysis system.

Embodiment 38: The method according to any one of the preceding method embodiments, wherein the method further comprises:

e) performing at least one analytical measurement by using the optical detector for detecting at least one detection reaction of at least one test chemical contained by the test element.

Embodiment 39: The method according to any one of the preceding method embodiments, wherein, in step d), the optical detector is moved towards the test element.

Embodiment 40: The method according to any one of the preceding method embodiments, wherein, after performing step b), the test field is out of focus with the optical detector, wherein, after performing step d), the test field is in focus with the optical detector.

In order that the embodiments of the present disclosure may be more readily understood, reference is made to the following examples, which are intended to illustrate the disclosure, but not limit the scope thereof.

FIG. 1A shows details of an exemplary embodiment of a test element analysis system 110 for the analytical examination of a sample in a perspective view. The test element analysis system 110 comprises a measurement device 112. The measurement device 112 comprises a test element receptacle 114 for receiving at least one test element 116. The test element receptacle 114 comprises at least one first part 118 and at least one second part 120.

The first part 118 may form a fixed subassembly 122 and the second part 120 may form a movable subassembly 124 of the test element receptacle 114. Specifically, the movable subassembly 124 may comprise at least one movable block 126. Further, the second part 120 comprises at least one optical detector 128 for detecting at least one detection reaction of at least one test chemical contained in the test element 116. The optical detector 128 may be inserted or integrated into the movable block 126. Specifically, the optical detector 128 may be inserted into at least one cavity 130 within the movable subassembly 124.

The second part 120 is movable relative to the first part 118, as will further be described below in more detail. Therefore, the test element analysis system 110 may comprise at least one actuator 132. The actuator 132 may be configured for driving a relative movement of the first part 118 and the second part 120. Specifically, the actuator 132 may be configured for performing a predetermined sequence of movements, sequentially bringing the second part 120 into the at least one position. Further, the actuator 132 may be configured for stopping a movement in the at least one position, respectively. Further, the test element analysis system 110 may comprise at least one controller 134 for controlling the predetermined sequence of movements. Furthermore, the test element receptacle 114 may comprise at least one guiding element 136 for guiding a relative movement of the second part 120 and the first part 118. Specifically, the guiding element 136 may comprise at least one guide rail 138, specifically at least one linear guide rail 140.

Figure 1B:
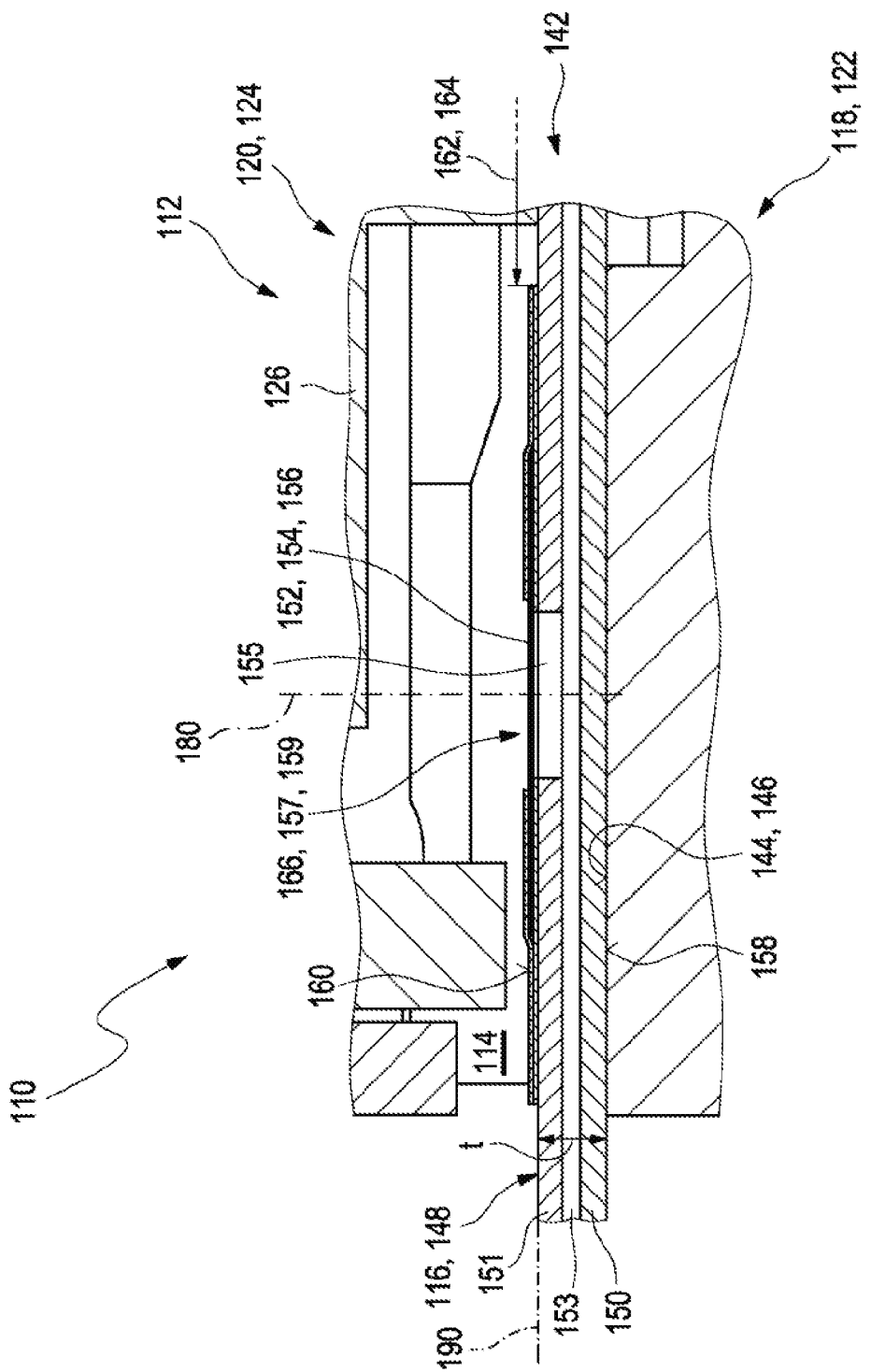

FIG. 1B shows a cross-sectional view of a part 142 of the test element analysis system 110 according to FIG. 1A. Specifically, in FIG. 1B, the test element 116 is illustrated. The test element 116 may lie on the first part 118. Specifically, the first part 118 comprises at least one support surface 144 for placement of the test element 116. The support surface 144 may specifically be an essentially flat surface 146.

The test element 116 may specifically be a test strip 148. Specifically, the test element 116 may have at least one carrier 150 and one cover 151 which form a capillary channel 153 which is able to transport the sample to the test field 152. The cover 151 may comprise an opening 155 to which a test chemical can be placed. Further, the test element may have at least one test field 152. The test field 152 may comprise at least one test chemical 154 for performing at least one detection reaction in the presence of an analyte contained in the sample. The test chemical 154 may be applied onto an additional element 157 which may be a transparent layer, e.g., a transparent foil 159. This transparent foil 159 may be mounted to the cover 151 in a manner that the test chemical 154 applied on the transparent foil 159 is facing towards the capillary channel 153 and placed in the opening 155 of the cover 151. This arrangement of the test field 152 comprising the test chemical 154 is advantageous for the following reasons: The test chemical 154 is placed is the same plane as the surface of the cover 151 facing the second part 120 and which is the contact surface for the abutment surface 184 of the second part 120. This arrangement results in a precise positioning of the test field 152 relative to the optical detector 128 which is independent of all other parts of the test element 116, like thickness of the carrier 150 or the cover 151 or thickness of the capillary channel 153. Additionally, a swelling and increase of the thickness of the test field 152 which may occur when the test chemical 154 is brought in contact with the sample for analytical detection will occur only in the direction towards the capillary channel 153. Because the optical focus of the optical detector 128 is defined by the surface of the cover 151 facing towards the second part 120, a swelling of the test field 152 in direction of the capillary channel 153 has no or only a reduced impact on the optical detection. The test field 152 may provide an optical detection area 166. The test chemical 154 may specifically be configured for performing at least one optically detectable detection reaction. The test chemical 154 may specifically be a dry test chemical 156. The test element 116 may have a reverse side 158. The reverse side 158 of the test element 116 may be configured to lie onto the support surface 144 of the first part 118. Further, the test element 116 may have a front side 160. At least one area 162 of the front side 160 of the test element 116 may be configured to serve as a reference area 164 for the second part 120 of the test element receptacle 114, as will further be described below in more detail. The reference area 164 may be formed by a part of the cover 151 which is facing towards the second part.

Figure 2:
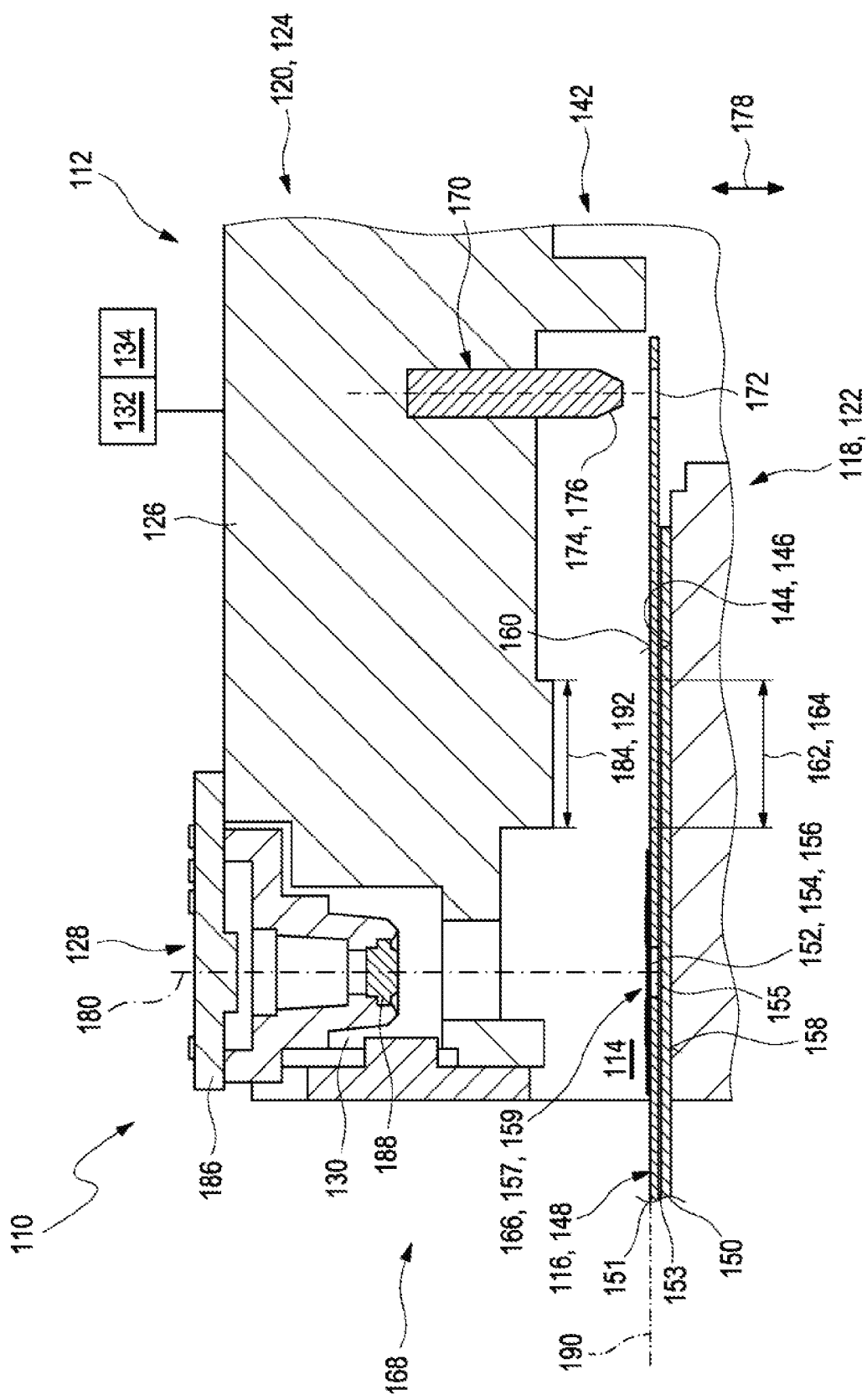
FIG. 2 shows details of an exemplary embodiment of a test element analysis system in a cross-sectional view.

In FIG. 2, a detail of a test element analysis system 110 is shown in a cross-sectional view. The test element analysis system 110 as depicted in FIG. 2 corresponds at least in large parts to the test element analysis system 110 as illustrated in FIGS. 1A and 1B. Thus, reference may be made to the description of FIGS. 1A and 1B above.

The test element receptacle 114 is configured to position the second part 120 in at least one position such that the test element 116 may be inserted into the test element receptacle 114. Thus, the test element analysis system 110, as illustrated in FIG. 2, shows the second part 120 in an open position 168. Thereby, the first part 118 and the second part 120 may be spaced apart such that the test element 116 may freely be inserted into the test element receptacle 114.

The second part 120 may further comprise at least one alignment pin 170 for engagement with at least one alignment hole 172 of the test element 116. The alignment pin 170 and the alignment hole 172 may have a round cross-section, respectively. Further, the alignment pin 170 may have a tip 174 specifically a tapered tip 176.

The optical detector 128 may be fixedly positioned within the second part 120. The second part 120 may be movable relative to the first part 118 in a direction 178 essentially perpendicular to the support surface 144. Further, the second part 120, specifically the optical detector 128 may be movable along an optical axis 180 of the optical detector 128.

Figure 3:
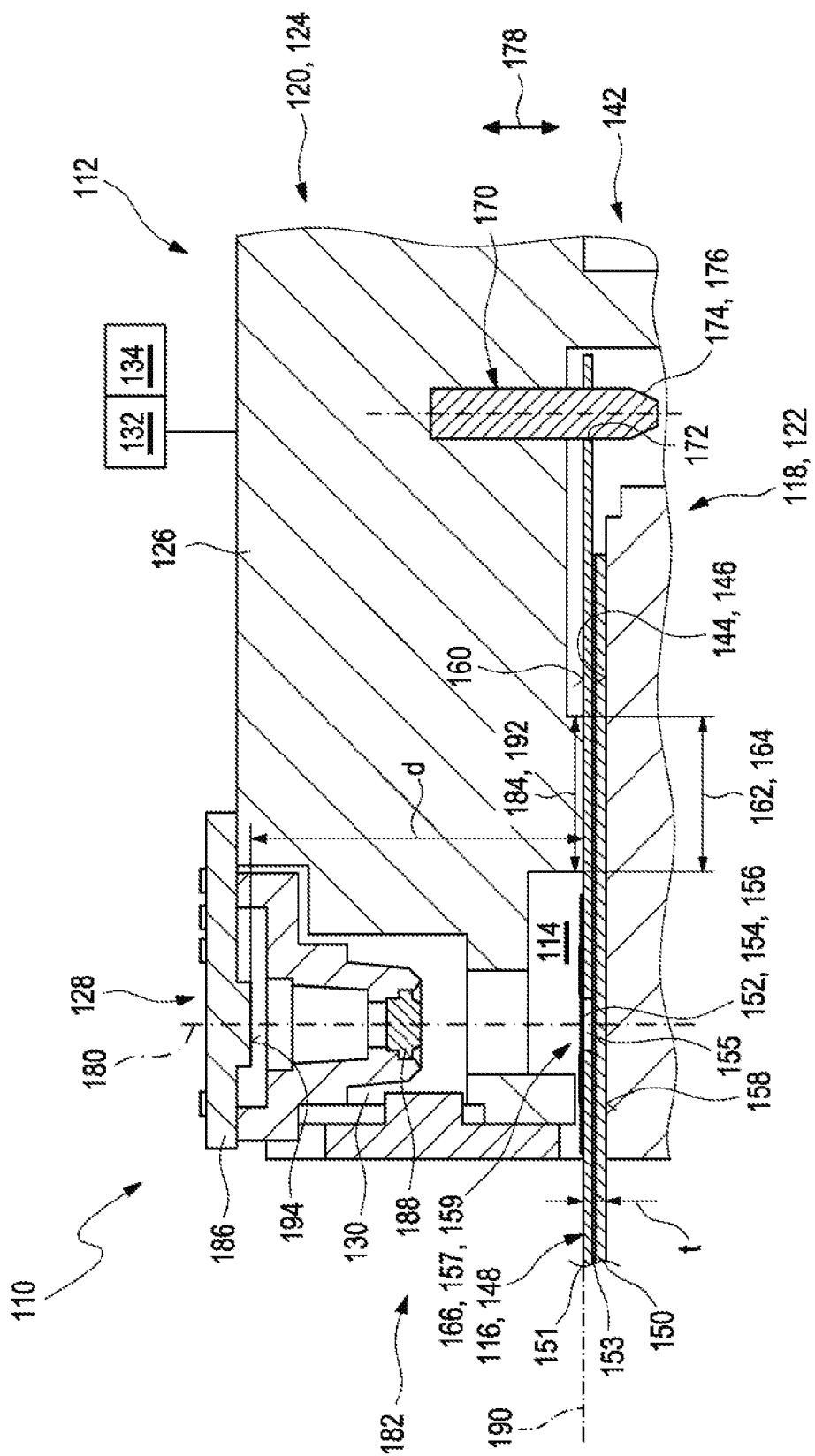
FIGS. 3A and 3B show details of an exemplary embodiment of a test element analysis system in a cross-sectional view (FIG. 3A) and in a perspective view (FIG. 3B)
Figure 3:
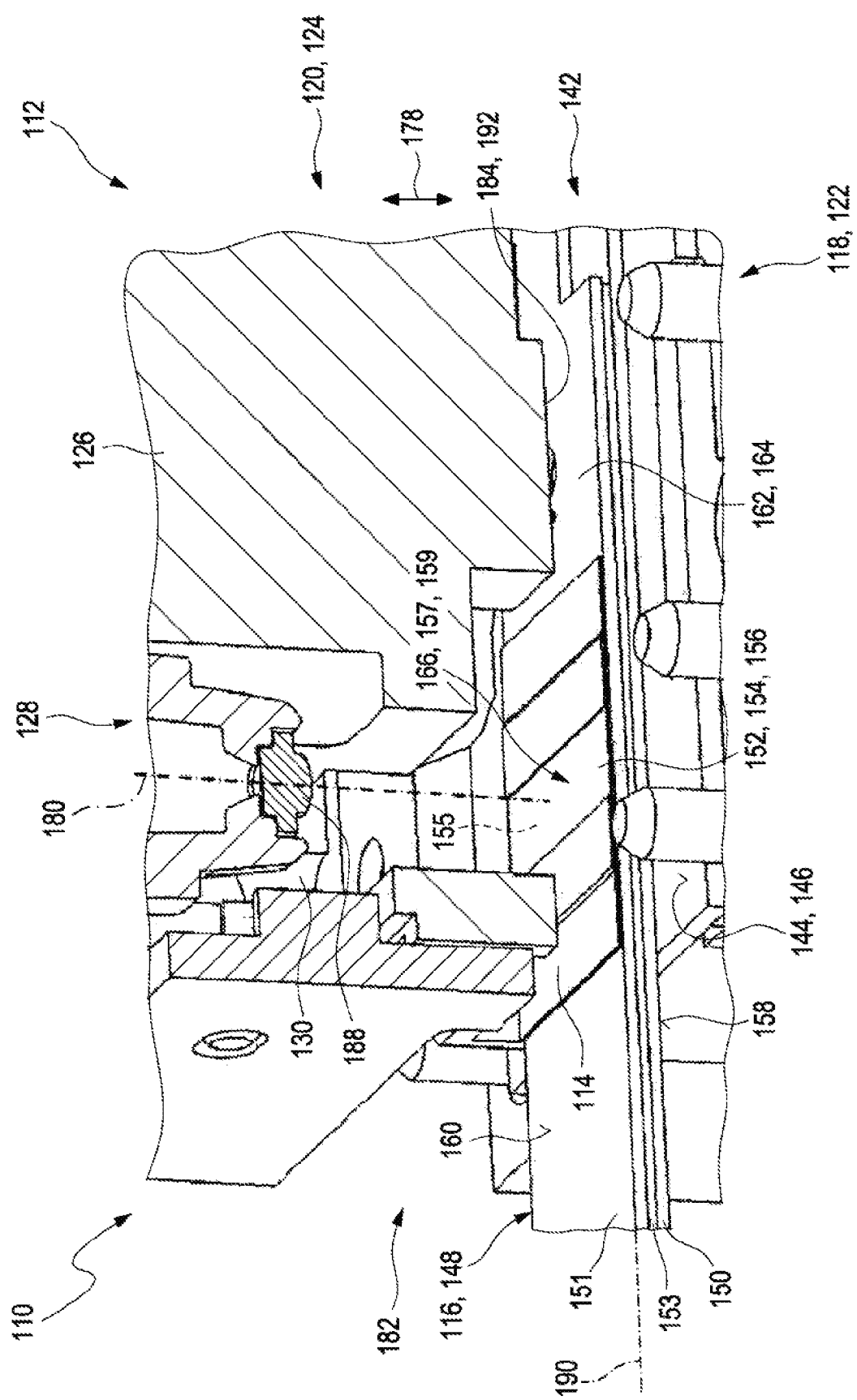

FIGS. 3A and 3B show details of an exemplary embodiment of the test element analysis system 110. In FIG. 3A, the test element analysis system 110 is illustrated in a cross-sectional view and in FIG. 3B, the test element analysis system is illustrated in a perspective view. The test element analysis system 110 as illustrated in FIGS. 3A and 3B corresponds at least in large parts to the test element analysis system 110 as illustrated in FIGS. 1A to 2. Thus, reference may be made to the descriptions of FIGS. 1A to 2 above.

As described above, the test element receptacle 114 is configured to position the second part 120 in at least one position. The test element receptacle 114 may be configured such that the test element 116 may be inserted into the test element receptacle 114, as illustrated in FIG. 2, and to subsequently close the test element receptacle 114, as illustrated in FIGS. 3A and 3B. Thus, the test element analysis system 110 is illustrated in a closed position 182. In the closed position 182, the first part 118 and the second part 120 may be arranged relative to each other, such that a removal of the test element 116 from the test element receptacle 114 is prevented at least to a large extent. Further, the test element analysis system 110 may be configured to perform a measurement when the second part 120 is in the closed position 182.

The second part 120 may comprise at least one abutment surface 184. The abutment surface 184 may be essentially parallel to the support surface 144. In the closed position 182, as depicted in FIGS. 3A and 3B, the abutment surface 184 of the second part 120 may rest on the test element 116. Specifically, in the closed position 182, the abutment surface 184 flatly rests on the test element 116, specifically on the cover 151 of the test element 116.

The optical detector 128 may comprise at least one photodetector 186. Further, the optical detector 128 may comprise at least one lens element 188. The lens element 188 may be located in front of the photodetector 186. Specifically, the abutment surface 184 may be located in a focal plane 190 of the lens element 188. Thus, the abutment surface 184 may also be referred to as optical detector reference area 192.

A distance d between the optical detection area 166 of the test element 116 and the optical detector, specifically of an optical detector area 194 of the optical detector 128 may be fixed. In the closed position, the test element 116 may therefore be independent of a thickness t. Variations in the thickness t of the test element 116 may specifically be not relevant for the optical detector 128.

Figure 4:
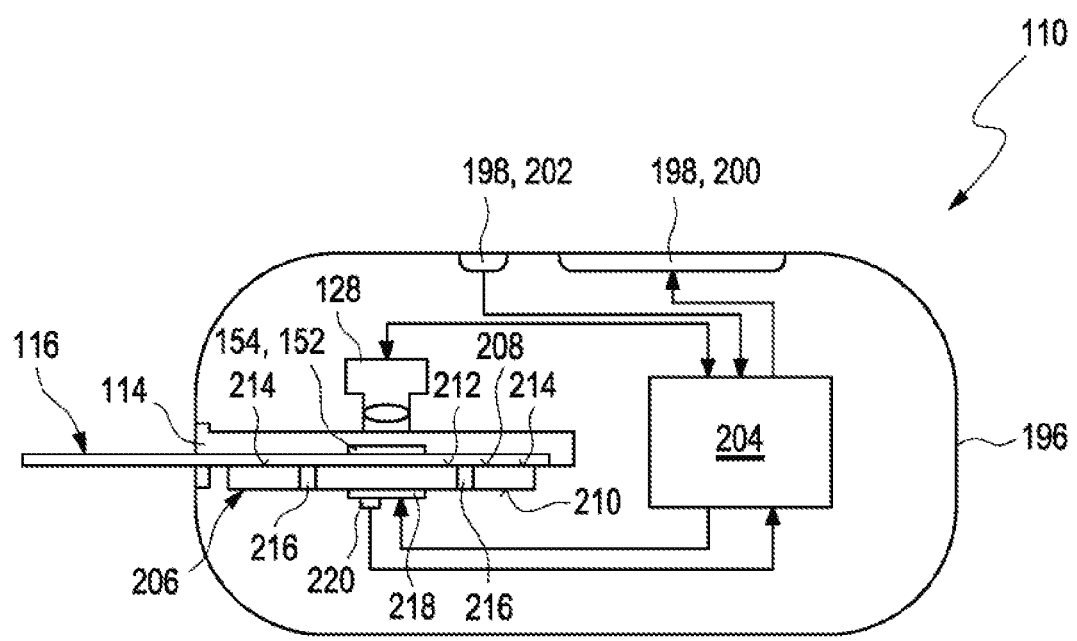
FIG. 4 shows details of an exemplary embodiment of a test element analysis system in a cross-sectional view.

In FIG. 4, details of a cross-sectional view of a simplified embodiment of a test element analysis system 110 for the analytical examination of a sample is shown. The test element analysis system 110 comprises a housing 196 with user interfaces 198, such as a display 200 and one or more control elements 202. The test element analysis system 110 comprises at least one controller 204 which, as an example, may fully or partially be configured as an evaluation device for evaluating the analysis. The controller 204 may be connected to the user interfaces 198.

The test element analysis system 110 further comprises the at least one test element receptacle 114 for receiving one or more of the test elements 116. The test element analysis system 110 further may comprise the at least one optical detector 128 for detecting at least one analytical reaction of the sample with the at least one test chemical 154 comprised by the test element 116, such as at least one test chemical 154 contained in at least one test field 152.

The test element 116 specifically may be designed as a test strip. The optical detector 128 may have at least one light source (not depicted) and at least one optical sensor, for performing remission measurements on the test field 152.

The test element analysis system 110 may further comprise at least one heating element 206 for heating the test element 116. The heating element 206 may comprise a front face 208, facing the test element 116, on which the test element 116 may rest, and, on an opposing side, a back face 210.

On the front face 208, an active area 212 may be defined which faces the region of the test element 116 containing the test field 152. Outside the active area 212, a non-active area 214 may be defined, as will be explained in further detail below. The active area 212 may be separated from the non-active area 214 by at least one thermal insulation element 216.

On the back face 210, the heating element 206 may comprise one or more heaters 218. Further, the heating element 206 may comprise one or more thermal sensor elements 220 for detecting a temperature of the heating element 206. The heater 218 and the thermal sensor element 220 may both directly or indirectly be connected to the controller 204.

LIST OF REFERENCE NUMBERS 110 test element analysis system
112 measurement device
114 test element receptacle
116 test element
118 first part
120 second part
122 fixed subassembly
124 moveable
126 moveable block
128 optical detector
130 cavity
132 actuator
134 controller
136 guiding element
138 guide rail
140 linear guide rail
142 part
144 support surface
146 essentially flat surface
148 test strip
150 carrier
151 cover
152 test field
153 capillary channel
154 test chemical
155 opening
156 dry test chemical
157 additional element
158 reverse side
159 transparent foil 160 front side
162 area
164 reference area
166 optical detection area
168 open position
170 alignment pin
172 alignment hole
174 tip
176 tapered tip
178 direction
180 optical axis
182 closed position
184 abutment surface
186 photo detector
188 lens element
190 focal plane
192 optical detector reference area
194 optical detector area
196 housing
198 user interface
200 display
202 control element
204 controller
206 heating element
208 front face
210 back face
212 active area
214 non-active area
216 thermal insulation element
218 heater
220 thermal sensor element

What is claimed is:

1. A test element analysis system for the analytical examination of a sample, comprising a measurement device, the measurement device comprising a test element receptacle for receiving at least one test element, wherein the test element receptacle comprises at least one first part and at least one second part, wherein the first part comprises at least one support surface for placement of the test element, wherein the second part comprises at least one optical detector for detecting at least one detection reaction of at least one test chemical contained in the test element, wherein the second part is movable relative to the first part, wherein the test element receptacle is configured to position the second part in at least one position such that a test element may be inserted into the test element receptacle and to subsequently position the second part in a closed position such that at least one abutment surface of the second part rests on the test element, wherein the test element analysis system further comprises at least one actuator for driving a relative movement of the first part and the second part, wherein the actuator is configured for performing a predetermined sequence of movements, sequentially bringing the second part into at least two positions, wherein the actuator is configured for stopping the movement in one of the at least two positions, respectively, and wherein the actuator is configured to move the second part towards the first part and to decouple as soon as the second part rests on the test element, wherein due to the decoupling of the actuator a contact pressure is defined by a weight of the second part, wherein the second part is moveable relative to the first part in a direction essentially perpendicular to the support surface, and wherein the second part further comprises at least one alignment pin for engagement with at least one alignment hole of the test element.

2. The test element analysis system according to the claim 1, wherein the optical detector comprises at least one lens element, wherein the abutment surface is located in one or both of a focal plane of the lens element and/or an essentially ideal object plane of the optical detector.

3. The test element analysis system according to the claim 2, wherein the optical detector comprises at least one light source and at least one photo detector, wherein the lens element is located in front of one or both of the at least one light source or the at least one photo detector.

4. The test element analysis system according to claim 1, wherein the optical detector is fixedly positioned within the second part.

5. The test element analysis system according to claim 1, wherein the test element analysis system further comprises at least one test element having at least one carrier and the at least one test chemical for performing at least one detection reaction in the presence of an analyte contained in the sample.

6. The test element analysis system according to claim 5, wherein the test chemical is a dry test chemical.

7. The test element analysis system according to claim 5, wherein the abutment surface flatly rests on the carrier when the abutment surface rests on the test element.

8. The test element analysis system according to claim 5, wherein, when the second part is moved relative to the first part, the abutment surface always is parallel to the support surface of the first part.

9. The test element analysis system according to claim 1, wherein the test element receptacle is configured to position the second part in at least two distinct positions relative to the first part, the at least two distinct positions comprising an open position for at least one of inserting the test element into the test element receptacle and removing the test element from the test element receptacle and a closed position for performing a measurement.

10. A method for analytical examination of a sample, the method comprising
   a) providing a measurement device having a test element receptacle for receiving at least one test element, wherein the test element receptacle comprises at least one first part and at least one second part, wherein the first part comprises at least one support surface for placement of the test element, wherein the second part comprises at least one optical detector for detecting at least one detection reaction of at least one test chemical contained in the test element, wherein the second part is movable relative to the first part and wherein the second part further comprises at least one alignment pin for engagement with at least one alignment hole of the test element, wherein the test element analysis system further comprises at least one actuator for driving a relative movement of the first part and the second part, wherein the actuator is configured for performing a predetermined sequence of movements, sequentially bringing the second part into at least two positions, wherein the actuator is configured for stopping the movement in one of the at least two positions, respectively, and wherein the actuator is configured to move the second part towards the first part and to decouple as soon as the second part rests on the test element;
   b) positioning the second part in a position such that a test element may be inserted into the test element receptacle;
   c) inserting the test element into the test element receptacle;
   d) closing the test element receptacle such that at least one abutment surface of the second part rests on the test element.

11. The method according to claim 10, wherein, after performing step b), the test field is out of focus with the optical detector, wherein, after performing step d), the test field is in focus with the optical detector.

* * * * *